United States Patent [19]

Baker et al.

[11] Patent Number: 5,259,012

[45] Date of Patent: Nov. 2, 1993

[54] LAMINOGRAPHY SYSTEM AND METHOD WITH ELECTROMAGNETICALLY DIRECTED MULTIPATH RADIATION SOURCE

[75] Inventors: Bruce D. Baker, Olivenhain; John A. Adams, Escondido; Robert L. Corey, San Diego, all of Calif.

[73] Assignee: Four PI Systems Corporation, San Diego, Calif.

[21] Appl. No.: 575,342

[22] Filed: Aug. 30, 1990

[51] Int. Cl.$^5$ .............................................. A61B 6/00
[52] U.S. Cl. .................................... 378/21; 378/137; 378/25; 378/22
[58] Field of Search ..................... 378/21, 22, 25, 99, 378/26, 23, 137, 121, 10, 143, 145; 250/370.1

[56] References Cited

U.S. PATENT DOCUMENTS

| | | | |
|---|---|---|---|
| 2,292,859 | 8/1942 | Allibone | 378/143 |
| 2,319,350 | 5/1943 | Schiebold | |
| 2,511,853 | 6/1950 | Kaiser | |
| 2,667,585 | 1/1954 | Gradstein | |
| 2,720,596 | 10/1955 | Acker | |
| 2,890,349 | 6/1960 | Huszar | |
| 2,998,518 | 8/1961 | Guntert | |
| 3,091,692 | 5/1963 | Verse | |
| 3,149,257 | 9/1964 | Elliott, Jr. | 378/10 |
| 3,499,146 | 3/1970 | Richards | 378/22 |
| 3,742,229 | 6/1973 | Smith et al. | 378/34 |
| 3,780,291 | 12/1973 | Stein et al. | 378/146 |
| 3,832,546 | 8/1974 | Morsell et al. | 378/28 |
| 3,843,225 | 10/1974 | Kock et al. | 378/2 |
| 3,894,234 | 7/1975 | Mauch et al. | 378/146 |
| 3,928,769 | 12/1975 | Smith | 378/22 |
| 3,962,579 | 6/1976 | Winnek | 378/41 |
| 3,984,684 | 10/1976 | Winnek | 378/41 |
| 4,002,917 | 1/1977 | Mayo | 378/14 |
| 4,007,375 | 2/1977 | Albert | 378/113 |

(List continued on next page.)

FOREIGN PATENT DOCUMENTS

| | | |
|---|---|---|
| 0225969 | 6/1987 | European Pat. Off. |
| 1138617 | 10/1962 | Fed. Rep. of Germany |
| 2946443 | 5/1981 | Fed. Rep. of Germany |
| 812792 | 5/1937 | France |
| 143290 | 11/1979 | Japan |
| 868830 | 5/1961 | United Kingdom |

OTHER PUBLICATIONS

Hasenkamp, "Radiographic Laminography," *Materials Evaluation*, Aug. 1974, pp. 169-180.

Moler, "Development of a Continuous Scanning Laminograph," Final Report No. IITRI V6034-24, Oct. 1968.

Blanche, "Nondestructive Testing Techniques for Multilayer Printed Wiring Boards," Nondestructive Test-
(List continued on next page.)

*Primary Examiner*—David P. Porta
*Assistant Examiner*—Kim-Kwok Chu
*Attorney, Agent, or Firm*—Dennis H. Epperson

[57] ABSTRACT

A tomographic inspection system which enables multiple locations within an object to be imaged without mechanical movement of the object. The object is interposed between a rotating X-ray source and a synchronized rotating detector. A focal plane within the object is imaged onto the detector so that a cross-sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions. Deflection voltage signals are applied to the X and Y deflection coils and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged. Changes in the radius of the X-ray source path result in a change in the Z level of the imaged focal plane.

20 Claims, 8 Drawing Sheets

U.S. PATENT DOCUMENTS

| | | | |
|---|---|---|---|
| 4,032,785 | 6/1977 | Green et al. | 378/61 |
| 4,075,489 | 2/1978 | Neal et al. | 378/10 |
| 4,107,563 | 8/1978 | Oddell | 378/126 |
| 4,130,759 | 12/1978 | Haimson | 378/10 |
| 4,139,257 | 2/1979 | Wintermute . | |
| 4,139,776 | 2/1979 | Hellstrom | 378/25 |
| 4,147,933 | 4/1979 | Rougeot et al. | 250/370.10 |
| 4,211,927 | 7/1980 | Hellstrom et al. | 378/26 |
| 4,228,353 | 10/1980 | Johnson | 378/6 |
| 4,234,792 | 11/1980 | DeCou et al. | 378/19 |
| 4,260,898 | 4/1981 | Annis | 378/146 |
| 4,340,816 | 7/1982 | Schott | 378/22 |
| 4,349,740 | 9/1982 | Grassmann et al. | 378/22 |
| 4,352,021 | 9/1982 | Boyd et al. | 378/12 |
| 4,385,434 | 5/1983 | Zehnpfennig et al. | 378/34 |
| 4,392,235 | 7/1983 | Houston | 378/137 |
| 4,400,620 | 8/1983 | Blum | 250/363.05 |
| 4,414,682 | 11/1983 | Annis et al. | 378/146 |
| 4,415,980 | 11/1983 | Buchanan | 378/58 |
| 4,426,722 | 1/1984 | Fujimura | 378/137 |
| 4,472,824 | 9/1984 | Buckley | 378/34 |
| 4,481,664 | 11/1984 | Linger et al. | 382/8 |
| 4,491,956 | 1/1985 | Winnek | 378/41 |
| 4,516,252 | 5/1985 | Linde et al. | 378/23 |
| 4,521,902 | 6/1985 | Peugeot . | |
| 4,618,970 | 10/1986 | Rand et al. | 378/137 |
| 4,628,531 | 12/1986 | Okamoto et al. | 382/8 |
| 4,688,241 | 8/1987 | Peugeot . | |
| 4,688,939 | 8/1987 | Ray | 356/237 |
| 4,730,350 | 3/1988 | Albert . | |
| 4,731,855 | 3/1988 | Suda et al. | 382/8 |
| 4,769,546 | 9/1988 | Kniffler et al. | 250/370.10 |
| 4,803,639 | 2/1989 | Steele et al. | 378/4 |
| 4,809,308 | 2/1989 | Adams et al. | 378/99 |
| 4,852,131 | 7/1989 | Armistead | 378/4 |
| 4,926,452 | 5/1990 | Baker et al. | 378/22 |
| 5,020,086 | 5/1991 | Peugeot . | |

OTHER PUBLICATIONS ing: Trends and Techniques, NASA SP-5082, 10/86, pp. 1-13.

Hamre, "Nondestructive Testing Techniques for Multilayer Printed Wiring Boards," Report No. IITRI-E60-24-15, Sep. 1965.

Kruger et al., "Industrial Applications of Computed Tomography at Los Alamos Scientific Laboratory," LA-8412-MS, Jun. 1980.

Stanley et al., "A New NDE Capability for Thin-Shelled Structures," AFWAL-TR-84-4120, Materials Lab, Wright Patterson AFB, Sep. 1984.

Deane et al., IRT Corp., "Using X-Ray Vision to Verify SMD-Board Quality," Electronic Test, Feb. 1987, pp. 32-35.

Soron, IRT Corp., "X-Ray Inspection Meets Increased PWB Throughput," Density Challenge—Part 1, Electronics, Oct. 1987, pp. 36-37.

Pound, "Image Processing Boosts the Power of Non-destructive Testing," Electronic Packaging and Production, Jun. 1985.

Casey, "X-Ray Inspection," *Manufacturing Systems*, Jul. 1987, p. 18ff.

Corey, IRT Corp., "Artificial Perception Gives Super Vision," *Research and Development*, Oct. 1984.

LaClair, "Nondestructive Measurement and Inspection Process," IBM Technical Disclosure Bulletin, vol. 18, No. 12, May 1976.

Hufault et al., "Lead-Indium Solder Joint Analysis," IBM Technical Disclosure Bulletin, vol. 19, No. 11, Apr. 1977.

Wittenberg, "IRT Improves SMT X-Ray Inspection System," *Electronic Engineering Times*, Oct. 5, 1987, p. 53.

Phelps, Christi, "Four Pi Captures Contract, Capital; Unveils Product," *San Diego Business Journal*, Week of Oct. 10-16, 1988.

LAMINOGRAPHY SYSTEM AND METHOD WITH ELECTROMAGNETICALLY DIRECTED MULTIPATH RADIATION SOURCE

FIELD OF THE INVENTION

The invention relates to computerized laminography, and, in particular, to systems which utilize multi-path laminography geometries for high speed, high resolution inspection.

BACKGROUND OF THE INVENTION

Laminography techniques are widely used to produce cross-section images of selected planes within objects. Conventional laminography requires a coordinated motion of any two of three main components comprising a laminography system (i.e., a radiation source, an object being inspected, and a detector). The coordinated motion of the two components can be in any of a variety of patterns, including linear, circular, elliptical and random patterns. Regardless of the pattern of coordinated motion selected, the configuration of the source, object and detector is such that any point in the object plane (i.e., the focal plane within the object) is always projected to the same point in the image plane (i.e., the plane of the detector), and any point outside the object plane is projected to a plurality of points in the image plane during a cycle of the pattern motion. In this manner, a cross-section image of the desired plane within the object is formed on the detector. The images of other planes within the object experience movement with respect to the detector thus creating a blur, i.e. background, on the detector upon which is superimposed the sharp cross-section image of the focal plane within the object. This technique results in sharp images of the desired object focal plane. Although any pattern of coordinated motion can be used, circular patterns are generally preferred because they are more easily produced.

The laminography techniques described above are currently used in a wide range of applications including medical and industrial X-ray imaging. Laminography is particularly well suited for inspecting objects which comprise several layers having distinguishable features within each layer. However, laminography systems which produce such cross-section images typically experience shortcomings in resolution and/or speed of inspection, thus accounting for its rare implementation. These shortcomings are frequently due to the difficulties in achieving high speed coordinated motion of the source and detector to a degree of precision sufficient to produce a high resolution cross-section image.

In a laminography system having a fixed object and a field of view which is smaller than the object being inspected, it may be necessary to move the object around within the field of view thus generating multiple laminographs which, when pieced together, cover the entire object. Movement of the object is frequently achieved by supporting the object on a mechanical handling system, such as an X, Y, Z positioning table. The table is then moved to bring the desired portions of the object into the field of view. Movement in the X and Y directions locates the area to be examined, while movement in the Z direction moves the object up and down to select the plane within the object where the image is to be taken. While this method effectively enables various areas and planes of the object to be viewed, there are inherent limitations associated with the speed and accuracy of such mechanical motions. These constraints effectively act to increase cycle time, thereby reducing the rates at which inspection can occur. Furthermore, these mechanical motions produce vibrations which tend to reduce the system resolution and accuracy.

SUMMARY OF THE INVENTION

The present invention comprises a laminography system which utilizes multipath scanning geometries which enable multiple locations on an object to be sequentially viewed without requiring mechanical movement of the object. Movement in various scan patterns produces laminographs at desired X, Y coordinate locations and various Z planes and with different size FOVs without the need for movement of the viewed object or mechanical movement of the source.

In accordance with the present invention, a laminography system is disclosed comprising a source of X-rays, an object to be viewed, and a detector. The X-ray source includes an electron gun which emits an electron beam incident upon a flat target anode. Focus and deflection coils direct the electron beam to specific locations on the target to form circular electron beam patterns on the surface of the target. When the electrons are slowed down or stopped in the target, Bremsstrahlung X-rays are generated. Since the electron beam describes a moving circular pattern on the target, the source of Bremsstrahlung X-rays also describes a moving circular pattern coincident with the electron beam pattern. In one embodiment, steering signals applied to the deflection coils cause the electron beam spot to rotate in a predetermined path in coordination with a similar path of the detector. In an alternative embodiment, a digital look-up-table (LUT) sends digital signals to the deflection coils which cause the beam spot to follow the circular motion of the electron beam on the target. In one embodiment which employs the LUT, digital addresses corresponding to the location of the X-ray detector along the circle traced by the detector are sent from the detector to the LUT. The LUT then sends deflection signals corresponding to specific detector positions to the electron beam deflection coils. The values of the deflection signals are calibrated to cause the X-ray source to trace a circular pattern upon the target which is precisely coordinated with the motion of the detector.

The source and detector rotate in synchronization about parallel axes of rotation such that an X-ray image of a desired region in a selected plane within the object is formed on the detector. The present invention provides a manner in which the image region and object plane of the image produced on the detector can be varied without physically moving the object. Rather, in one embodiment, an offset signal is applied to the deflection coils which acts to shift the center of rotation of the electron beam on the target thus causing a different region at a different X, Y location of the object to be imaged upon the detector. In a preferred embodiment, this offset signal is incorporated with the deflection signals transmitted from the LUT to the deflection coils. In one embodiment, the deflection coils comprise X and Y deflection coils, and the path traced by the beam spot is circular. Applying a constant voltage offset to either the X or Y deflection coil effects a linear shift in the center of the circle traced by the rotating beam spot, thereby shifting the image region in the X or Y direction along the selected object plane within the viewed object. The amplitude of the constant voltage offsets applied to the coils determines the direction and amount of the shift in the image region of the object plane.

In addition, with the present invention, the location of the image object plane within the object can be varied in the Z direction, again without movement of any of the system components. This is achieved by a gain adjustment which simultaneously changes the amplitudes of the deflection signals applied to both deflection coils, thus causing the radius of the scan circle traced by the beam spot on the target to vary by an amount proportional to the change in amplitudes of the deflection signals.

Thus, the present invention provides a laminography system wherein X, Y scanning and Z height scanning is accomplished with no physical movement of the system components. Elimination of physical movement advantageously decreases cycle time of the system while further eliminating other adverse effects associated with mechanical movement of the components.

In accordance with the present invention, a laminography system is disclosed comprising a source of X-rays adapted for emitting X-rays from a moving point wherein the point describes a predetermined path about a designated first location. A planar X-ray detector is adapted to move along a predetermined path which is coordinated with the predetermined path of the X-ray source to produce a laminographic image of a first portion of an image plane within an object being inspected. A control system shifts the location of the X-ray source designated location to a second designated location, thereby producing a laminographic image of a second portion of the image plane within the object without altering either the position of the object or the path of the detector. The predetermined path of the X-ray source may be circular, wherein the first designated point is the center of rotation of the circular path. The control system may further comprise a look-up-table (LUT).

The present invention provides a laminography system comprising a source of X-rays which travels along a predetermined first circular path about a center of rotation wherein the circular path has a first radius. An X-ray detector is coordinated with the X-ray source so that a field of view is defined in an object plane wherein a cross-section image of an object placed in the field of view is produced by the detector. A control system causes the X-ray source to rotate in a second circular path about the center of rotation, wherein the second circular path has a second radius, thereby shifting the location of the field of view. The control system may further comprise a look-up-table (LUT).

A method for producing a laminographic image is disclosed comprising the steps of moving a source of X-rays along a predetermined path about a designated point, coordinating an X-ray detector with the X-ray source so that a field of view is defined in an object plane wherein a cross-sectional image of an object placed in the field of view is produced by the detector, and shifting the designated point about which the X-ray source travels, thereby shifting the location of the field of view in the object plane. The X-ray source may be moved in a circular path, wherein the designated point is defined as the center of rotation of the circular path.

Additionally, a method of producing a laminographic image is disclosed comprising the steps of moving a source of X-rays along a predetermined first circular path about a center of rotation, wherein the first circular path has a first radius, coordinating an X-ray detector with the X-ray source so that a field of view is defined in an object plane wherein a cross-sectional image of an object placed in the field of view is produced by the detector, and causing the X-ray source to rotate in a second circular path about the center of rotation, wherein the second circular path has a second radius, thereby shifting the location of the field of view.

In another aspect of the invention, a laminography system is disclosed comprising a moving source of X-rays, and a moving planar X-ray detector adapted to move in coordination with the X-ray source. Means for supporting an object to be inspected in a stationary position are located between the X-ray source and the detector. A control system comprises a driver for driving the X-ray source along a predetermined path, and a coordinator for coordinating the motion of the X-ray source with that of the detector in a manner which produces a laminographic image having a field of view in an object plane of the object under inspection. The control system further comprises a field of view shifter for altering the predetermined path followed by the X-ray source, thereby moving the field of view and producing a laminographic image of a different portion of the object.

In yet another aspect of the invention, a laminography system is disclosed comprising a source of X-rays adapted for emitting X-rays from a moving point which describes a first circular path about a center of rotation, wherein the first circular path has a first radius. A planar X-ray detector is adapted to move along a predetermined path which is coordinated with the circular path of the X-ray source to produce a laminographic image of a portion of a first image plane within an object being inspected. A control system causes the X-ray source to rotate in a second circular path about the center of rotation, wherein the second circular path has a second radius, thereby producing a laminographic image of a portion of a second image plane within the object without altering either the position of the object or the path of the detector.

In accordance with the present invention, a laminography system is disclosed comprising a source of electrons for producing a beam of electrons and a deflector for deflecting the beam of electrons. A target converts the beam of electrons into an X-ray source and has a plurality of concentric rings. An X-ray detector is coordinated with the X-ray source to produce a laminographic image of a portion of an image plane within an object to be inspected. The system further comprises a control system capable of causing the deflector to deflect the beam of electrons onto the target so that a selected circular path, corresponding to one of the concentric rings of the target, is traced by the X-ray source, thereby producing a laminographic image of a portion of the image plane within the object, without altering the position of the object or the path of the detector, the position of the image plane being determined by the selected path of the X-ray source.

In yet another aspect of the invention, an X-ray tube is disclosed comprising a source of electrons for producing a beam of electrons and a deflector for deflecting the beam of electrons. A target converts the beam of electrons into an X-ray source and has a plurality of concentric rings. A control system causes the deflector to deflect the beam of electrons onto the target so that a selected circular path, corresponding to one of the concentric rings of the target, is traced by the X-ray source.

In a further aspect of the invention, a laminography system is disclosed comprising a source of electrons for producing a beam of electrons, and a deflector for deflecting the beam of electrons. A target converts the beam of electrons into an X-ray source and is formed to have a cylindrical interior surface. An X-ray detector is coordinated with the X-ray source to produce a laminographic image of a portion of a first image plane within an object to be inspected. A control system causes the deflector to deflect the beam of electrons onto the cylindrical interior surface of the target so that a circular path may be traced at a selected location along the interior surface of the target, thereby producing a laminographic image of a portion of an image plane within the object without altering the position of the object or the path of the detector, the position of the image plane being determined by the selected location of the circular path of the X-ray source.

Additionally, an X-ray tube is disclosed comprising a source of electrons for producing a beam of electrons and a deflector for deflecting the beam of electrons. A target converts the beam of electrons into an X-ray source and is formed to have a cylindrical interior surface. A control system causes the deflector to deflect the beam of electrons onto the cylindrical interior surface of the target so that a circular path may be traced at a selected location along the interior surface of the target.

DETAILED DESCRIPTION OF THE INVENTION

Figure 1:
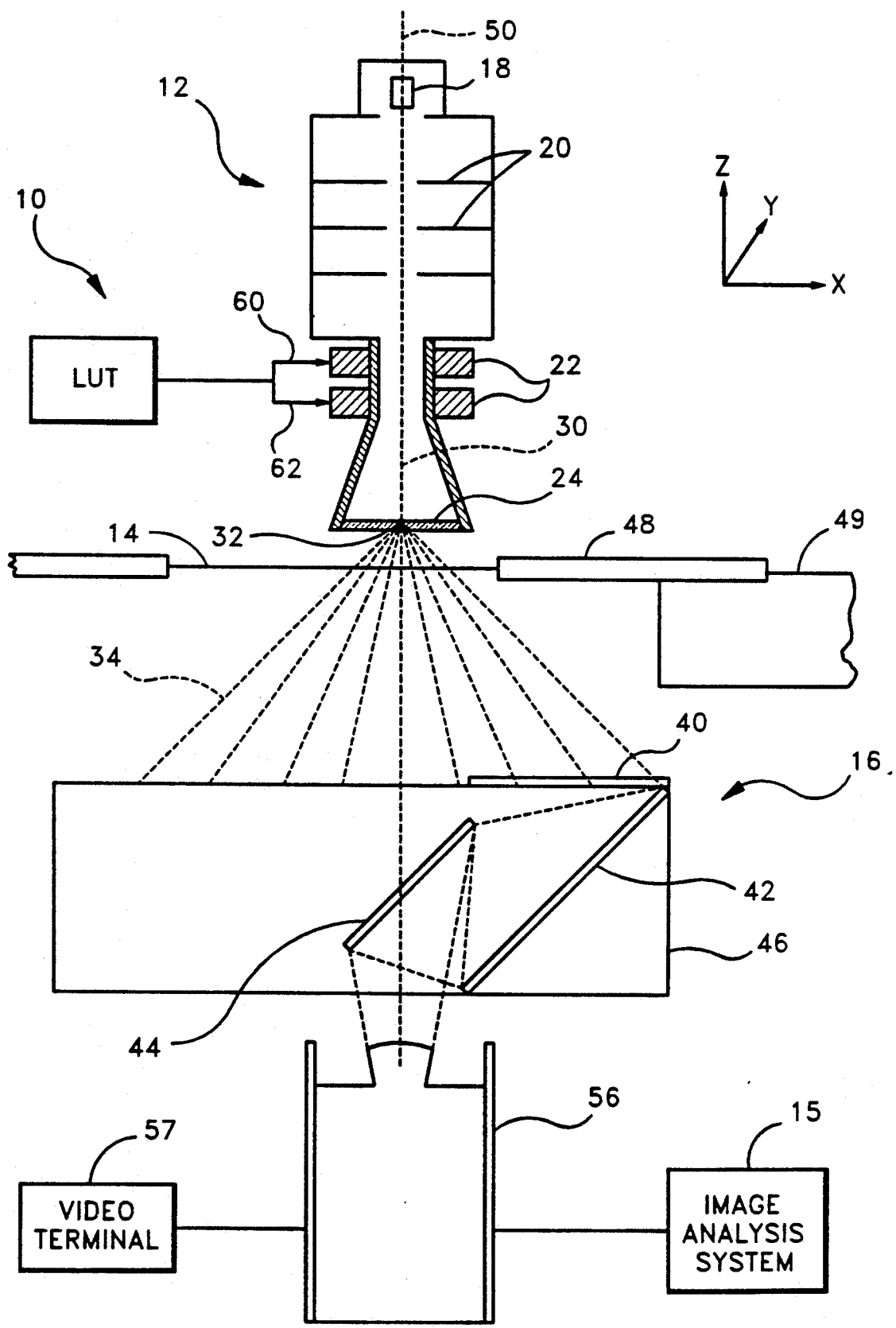
FIGS. 1 and 2 are schematic views of a laminography system in accordance with the present invention.

FIG. 1 illustrates a schematic diagram of a laminography system 10 in accordance with the present invention. The system 10 comprises a source of X-rays 12 positioned above an object 14 to be viewed, and a rotating X-ray detector 16, positioned below the object 14, opposite the X-ray source 12. The object 14 may, for example, be an electronic item such as a circuit board, a manufactured item such as an aircraft part, a portion of a human body, etc.

The invention acquires X, Y plane cross-sectional images of the object 14 under inspection using multipath laminography geometries which enables multiple locations of the object 14 to be sequentially viewed without requiring mechanical movement of the object 14. Movement in various scan circles produces laminographs at the desired X, Y coordinate locations and various Z planes without the need for movement of the viewed object 14. In one embodiment, the invention may be interfaced with an analysis system 15 which automatically evaluates the cross-section image generated by the system 10 and provides a report to the user that indicates the results of the evaluation.

The source 12 is positioned adjacent the object 14, and comprises an electron gun 18, a set of electrodes for electron beam acceleration and focus 20, a focus coil 60, and a steering yoke or deflection coil 62, and a substantially flat target anode 24. An electron beam 30 emitted from the electron gun 18 is incident upon the target anode 24, producing an X-ray spot 32 which serves as an approximately point source of X-rays 34. The X-rays 34 originate in the target anode 24 from the point where the electron beam 30 impinges upon the target anode 24 and, as described below, illuminate various regions of the object 14.

The object 14 is typically mounted on a platform 48 which may be affixed to a granite table 49, so as to provide a rigid, vibration-free platform for structurally integrating the functional elements of the system 10, including the X-ray source 12 and turntable 46. It is also possible that the platform 48 comprises a positioning table that is capable of moving the object 14 relatively large distances along three mutually perpendicular axes X, Y, and Z.

The rotating X-ray detector 16 comprises a fluorescent screen 40, a first mirror 42, a second mirror 44, and a turntable 46. The turntable 46 is positioned adjacent to the object 14, on the side opposite to the X-ray source 12. A camera 56 is positioned opposite the mirror 44, for viewing images reflected into the mirrors 42, 44 from the fluorescent screen 40. The camera 56 typically comprises a low light level closed circuit television camera that produces a video image of the X-ray image formed on the fluorescent screen 40. The camera 56 may, for example, be connected to a video terminal 57 so that an operator may observe the image appearing on the detector 40. The camera 56 may also be connected to the image analysis system 15.

The laminography system 10 is advantageously encased by a supporting chassis (not shown) which acts to prevent undesired emissions of X-rays, as well as facilitating the structural integration of the major elements of the system 10.

In operation, X-rays 34 produced by the X-ray source 12 illuminate and penetrate regions of the object 14 and are intercepted by the screen 40. Synchronous rotation of the X-ray source 12 and detector 16 about an axis 50 causes an X-ray image of a plane 52 (see FIG. 2) within the object 14 to be formed on the detector 16. Although the axis of rotation 50 illustrated is the common axis of rotation for both the source 12 and detector 16, one skilled in the art will recognize that it is not necessary for the axes of rotation to be collinear. In practice, it is sufficient that the axes of rotation be parallel. X-rays 34 which penetrate the object 14 and strike the screen 40 are converted into visible light reflected by the mirrors 42, 44 and into the camera 56.

Figure 2:
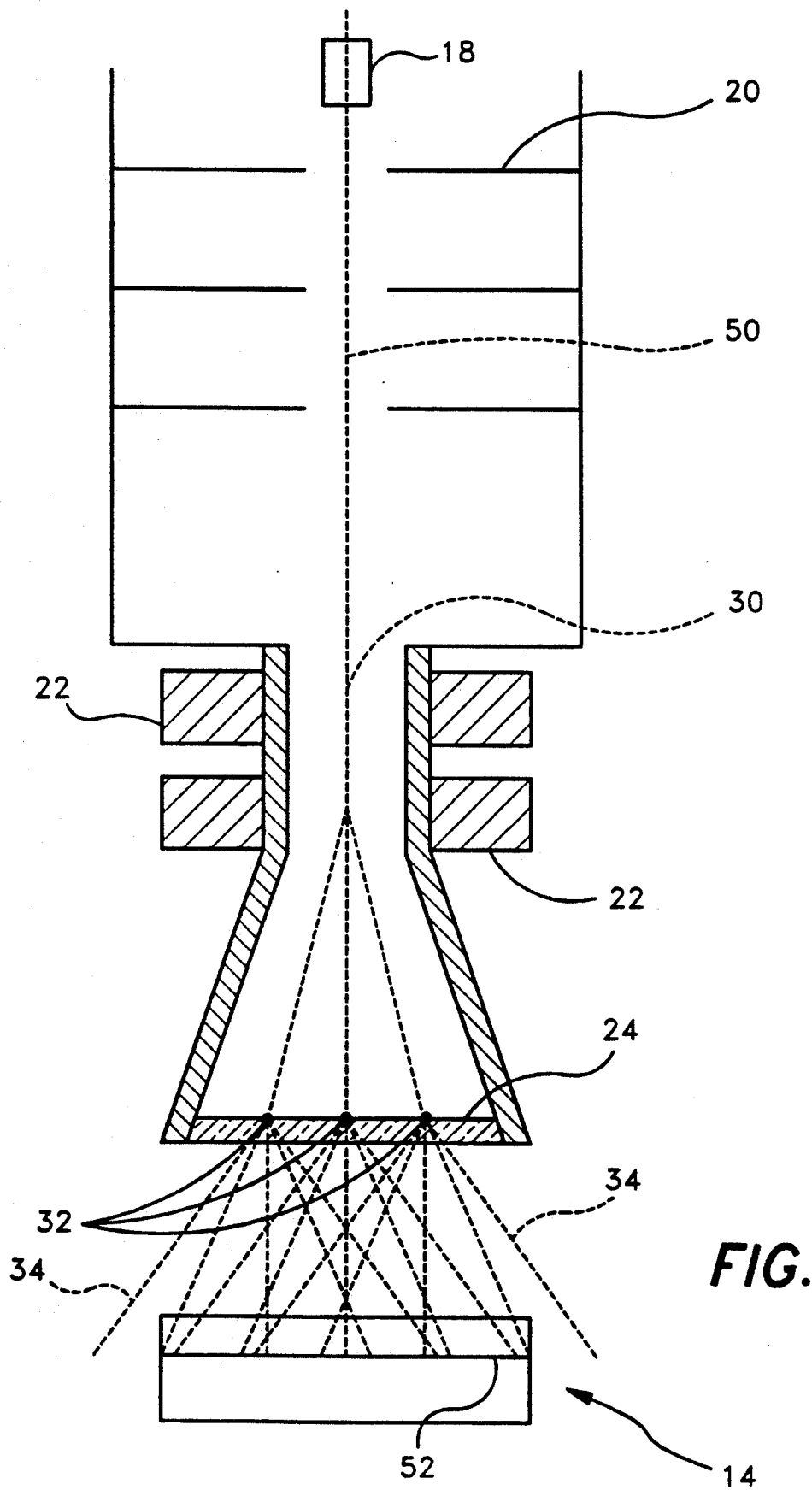

Referring to FIG. 2, the electron beam 30 is emitted from the electron gun 18 and travels in a region between the electrodes 20 and steering coils 22. The electrodes 20 and coils 22 produce electromagnetic fields which interact with the electron beam 30 to focus and direct the beam 30 onto the target anode 24 forming an electron beam spot 32 from which X-rays are emitted. Preferably, the size of the electron beam spot 32 on the target is on the order of 0.02 to 10 microns in diameter. The steering coils 22 enable the X-ray source 12 to provide X-rays 34 from the X-ray spots 32 wherein the location of the spots 32 move in a desired pattern around the target anode 24.

Preferably, the steering coils 22 comprise separate X and Y electromagnetic deflection coils 60, 62 which deflect the electron beam 30 discharged from the electron gun 18 in the X and Y directions, respectively. Electrical current flowing in the steering yoke 62 creates a magnetic field which interacts with the electron beam 30 causing the beam 30 to be deflected. However, one skilled in the art will also recognize that electrostatic deflection techniques could also be used to deflect the electron beam 30. Preferably, an LUT 63 outputs voltage signals which, when applied to the X and Y deflection coils 60, 62 cause the electron beam spot 32 to rotate, thus producing a circular pattern on the surface of the target anode 24. In one embodiment, the LUT 63 provides the output voltages in response to addressing signals from a master computer (not shown) which may be included within the image analysis system 15. The output voltages are advantageously predetermined using a calibration technique which correlates the position of the turntable 46, and the position of the X-ray beam spot 32.

The present invention provides a method and apparatus for processing laminographic images of various regions of the object 14 which requires little or no physical movement of the object 14 or the supporting table 48. In accordance with the present invention, desired regions of the object are brought within the field of view of the system by moving the location of the field. This is accomplished by moving the location of the pattern traced by the X-ray beam spot 32 on the target anode 24. In this manner, various portions of the object 14 are brought within the field of view and images are produced of that portion of the object coinciding with the field of view. In accordance with the present invention, the voltages applied to the X and Y deflection coils 60, 62 are varied in order to produce rotating X-ray beam paths of distinct radii having distinct x, y locations on the target anode 24.

Figure 3A:
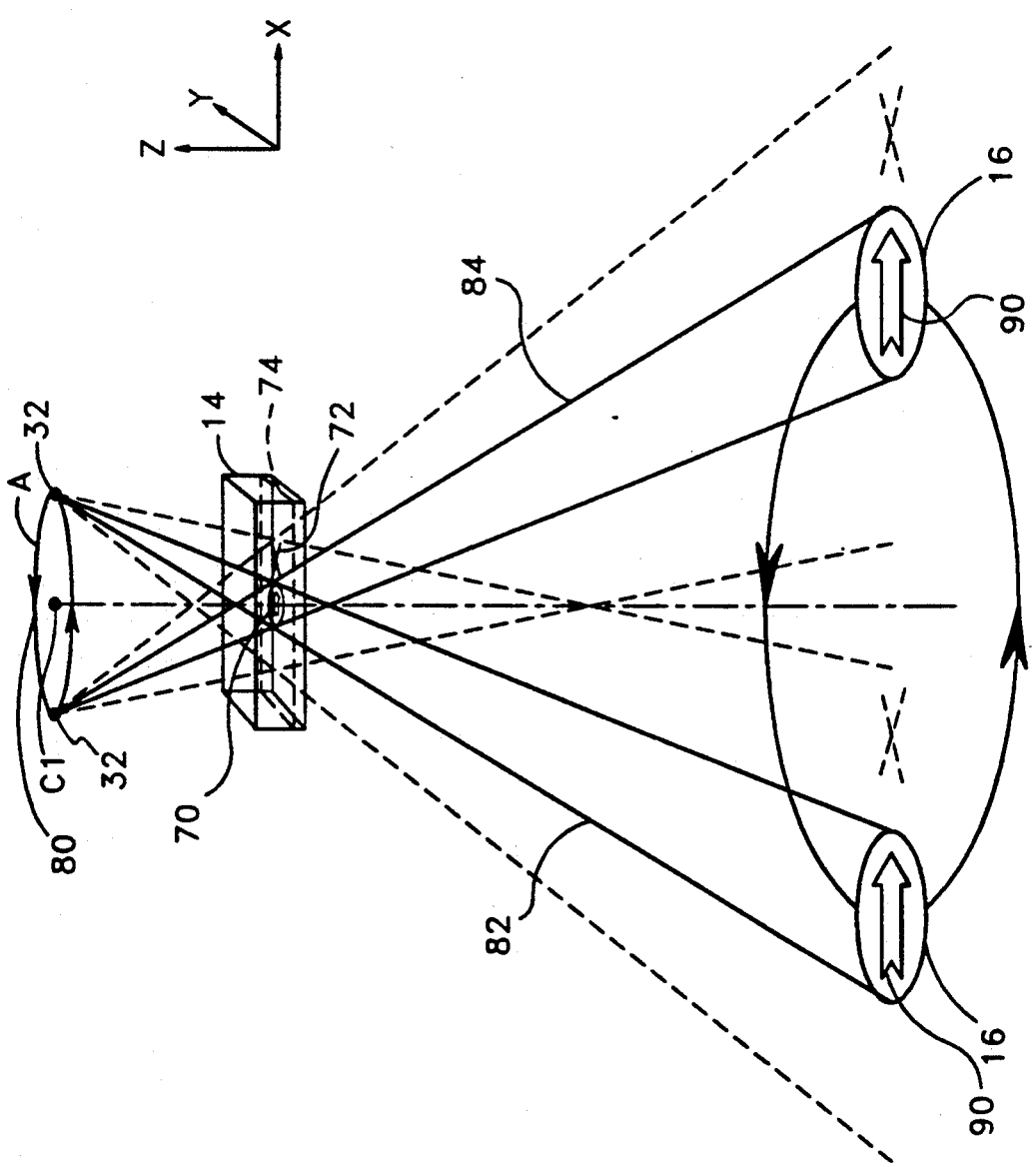
FIGS. 3a and 3b illustrate the manner in which a laminographic system in accordance with the present invention is utilized to produce an X-Y axis shift of the image region within the object.

FIG. 3a illustrates the laminography geometry and technique used to image different x, y regions of the object by electronically moving the center of rotation of the rotating X-ray source on the X-ray source target. The rotating spot 32 of X-rays 34 formed in the manner described above is positioned above the object 14 to be viewed. For purposes of illustrating the operation of the invention, the object 14 contains the patterns of an arrow 70 and a cross 72 located within different regions of an internal plane 74 of the object. As previously described, signals from the LUT 63 can be applied to the X and Y deflection coils 60, 62 (FIG. 2) so as to cause the X-ray spot 32 to trace a circular path on the target anode 24. In the position labelled A (FIG. 3a), a scan circle 80 having a center C1 is produced which emits X-rays 34 incident upon the object 14. As the X-ray spot 32 and detector 16 rotate in synchronization as described above, the X-rays 34 are emitted in diverging beams at each point along the scan circle 80, forming a family of cones or conical regions wherein each cone has an apex defined by the X-ray spot 32 and a base defined by the detector assembly 16. Two cones 82, 84 defined by the X-ray spot 32 and detector 16 at two different locations along the circular path of the scan circle 80 are shown. The intersection of the conical regions around a complete rotation of the X-ray spot 32 and detector 16 defines a set of points which comprise the field of view. Thus, the portion of the object plane which coincides with the field of view is imaged by the detector 16. As illustrated, the intersection of the cones 82, 84 produced by the rotating X-ray spot 32 and detector 16 is substantially centered about the arrow pattern 70 in the internal plane 74. Thus, the region imaged when the X-ray source 32 traces the scan path 80 includes the arrow pattern 70, and the object, or focal plane is the internal plane 74. In this manner, the rotating X-ray spot 32 and detector 16 produce a distinct image 90 of the arrow upon the detector 16.

Because the cross pattern 72 lies outside the field of view defined by the intersecting cones 82 and 84 when the path 80 is traced by the electron beam 30, the image of the cross pattern 72 does not fall on the detector 16 at any time during the rotation of the detector 16 and thus, does not form an image on the detector 16.

Figure 3B:
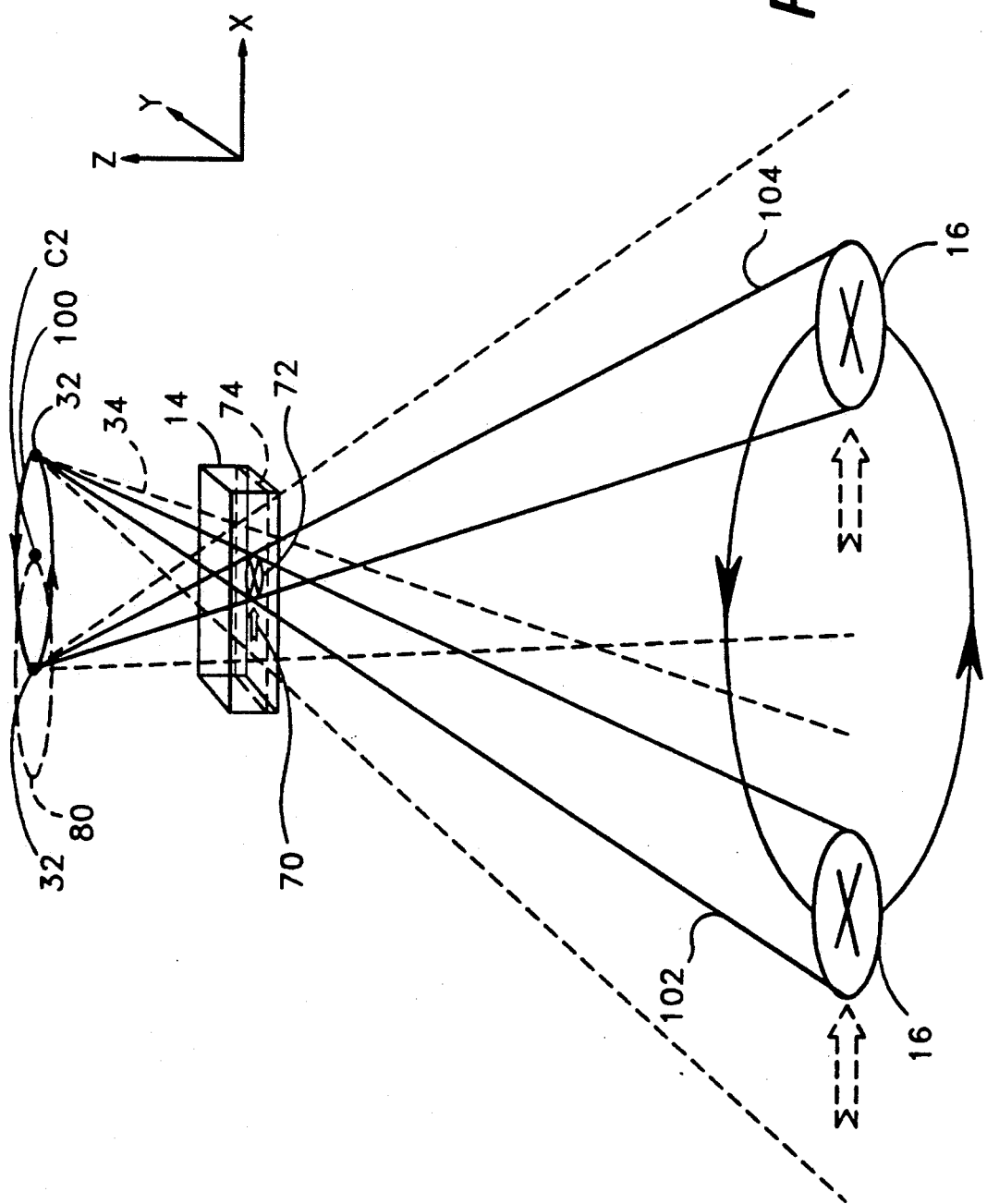

Application of an offset voltage to the X and/or Y deflection coils 60 and/or 62 acts to shift the path traced by the X-ray source 32, as shown in FIG. 3b, such that a scan circle 100 having a center C2 is traced by the X-ray spot 32 on the target anode 24. As the X-ray spot 32 rotates about the circle 100, a second family of cones, illustrated by the two cones 102, 104, intersects the object plane 74 and defines a field of view substantially centered about the cross pattern 72. Thus, a new field of view, which is linearly displaced from the original field of view shown in FIG. 3a, is defined when the path traced by the X-ray source 32 has its center of rotation shifted in the X and/or Y directions from center of rotation C1 to center of rotation C2.

The arrow pattern 70 now lies outside the field of view in the object plane 74 such that, as the X-ray spot 32 and detector 16 rotate, a cross-sectional image of the cross pattern 72 is produced on the detector 16, and the image of the arrow 70 does not appear. The amplitude of the offset applied to the deflection coils 60, 62 is proportional to the distance and direction the path traced by the X-ray spot 32 is shifted, i.e., the distance and direction that the center of the scan circle is shifted. Thus, the laminography geometry of the present invention enables different regions of the object 14 to be viewed and imaged upon the detector 16 without any physical movement of the source 12, object 14, or detector 16. Furthermore, any vibrations or other adverse effects resulting from mechanical movement of the system components are eliminated, thereby increasing the speed and accuracy of the system 10.

It should be noted that shifting the position of the path traced by the X-ray source 32 results in a change in the distance of the path followed by the electron beam 30 (FIGS. 1 and 2). That is, the distance from the cathode filament to the target surface changes each time a shift is effected in the position of the X-ray spot 32 (which coincides with the electron spot on the target anode 24). This results in a change in the focal length of the electron beam 30, so that dynamic focusing of the beam must be brought about in order to maintain a sharp focal point of the electrons within the beam 30 at the surface of the target anode 24. Thus, the present invention advantageously effects a change in voltage applied to the focusing coil that is appropriate to maintain the focal point of the beam 30 at the surface of the target anode 24.

Figure 4A:
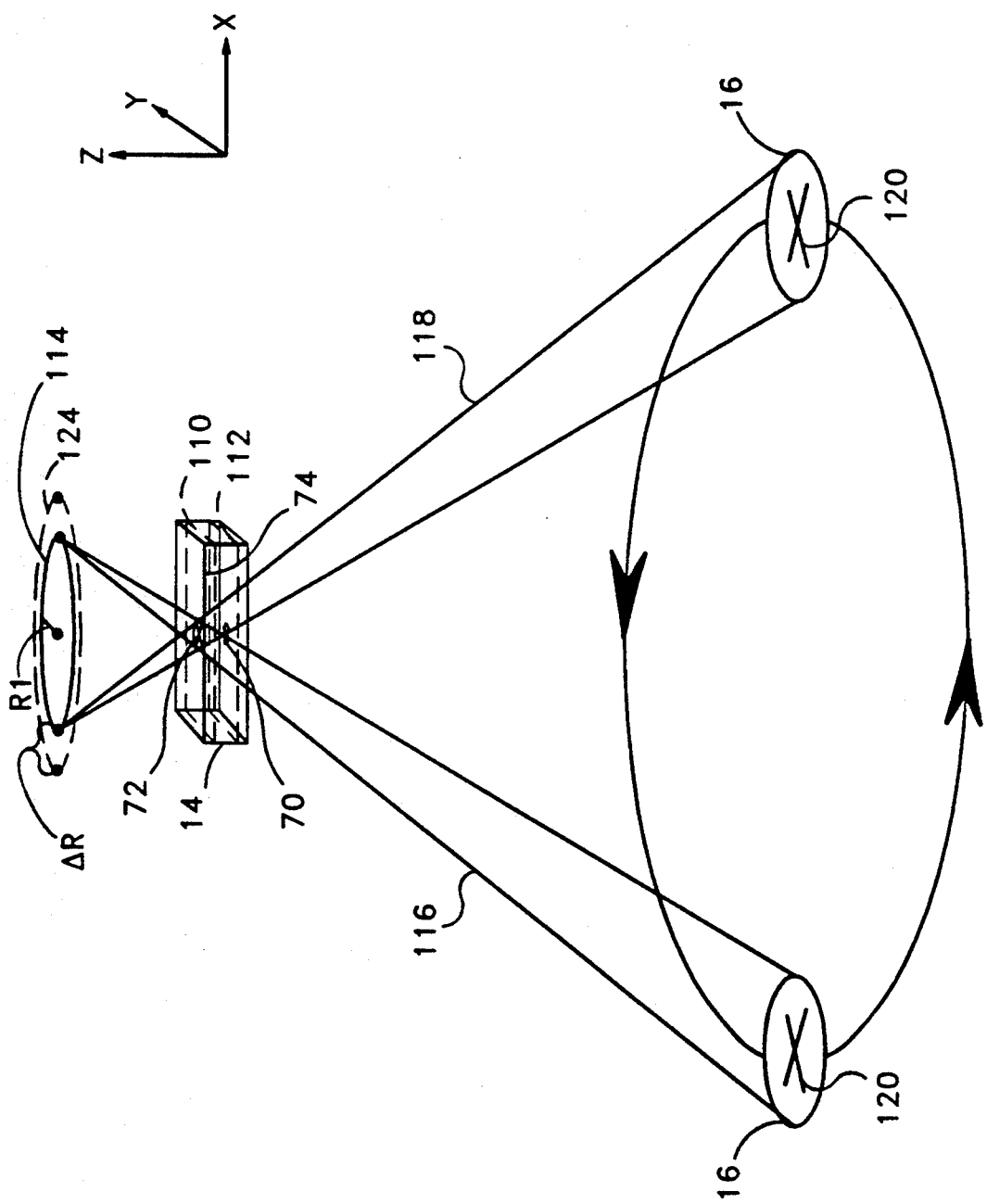
FIGS. 4a and 4b illustrate the manner in which a laminographic system in accordance with the present invention is utilized to produce a Z-axis shift of the imaged region of the object plane within the object.
Figure 4B:
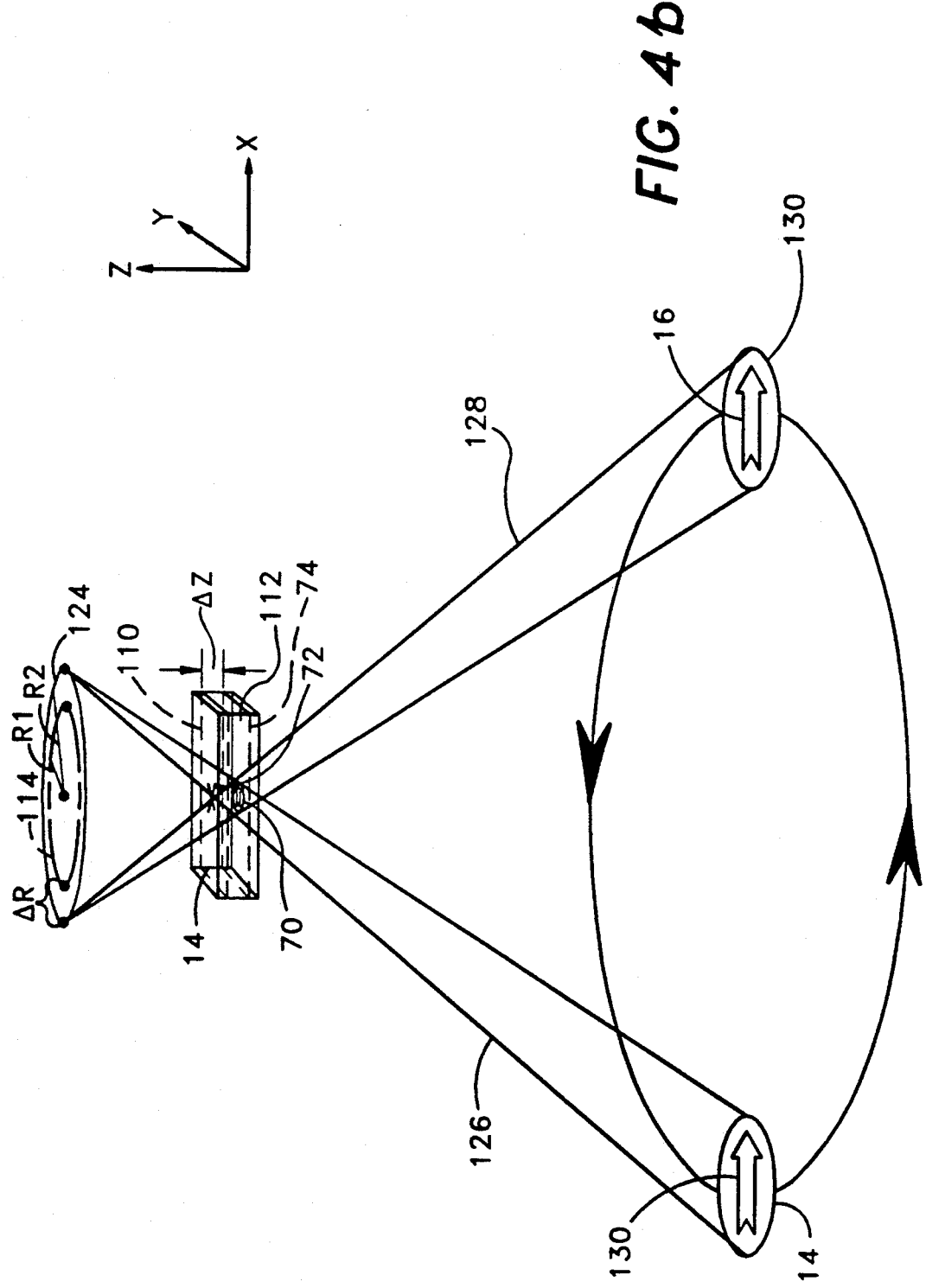

Referring to FIG. 4a and FIG. 4b, the present invention further provides a laminography system having a geometry which can be utilized to effect a shift or change in the object plane 74. FIG. 4a illustrates an object 14 having the patterns of an arrow 70 and a cross 72 located therein. The cross pattern 72 is located in a first plane 110 and the arrow pattern 70 is located in a second plane 112, wherein the first plane 110 lies above and is parallel to the second plane 112. The X-ray beam spot 32 traces a scan circle 114 having a radius R1, defining a family of cones including cones 116, 118. The intersection of the cones around the circle 114, including cones 116, 118, forms an image region substantially centered about the cross pattern 72, such that the first plane 110 is defined as the object plane 74. As the X-ray spot 32 and detector 16 rotate in synchronization, a distinct image 120 of the cross pattern 72 is produced on the surface of the detector 16. The image of the arrow 70, which lies in the second plane 112 and is outside the object plane 74 defined by the cones 116, 118, is not stationary on the detector 16 during the entire rotation of the detector 16 and thus, appears blurred.

FIG. 4b illustrates that by equally adjusting the gain of the voltages output from the LUT 63 to both deflection coils 60, 62, thereby changing the amplitude of the sine and cosine signals, the radius of the scan circle traced by the X-ray spot 32 can be varied to produce images of regions within distinct planes in the object 14. With the adjustment of the gain applied to the output from the LUT 63, the scan circle 114 is increased in radius by a value $\Delta R$ to a radius R2, thereby forming a scan circle 124 defining a second family of cones including the cones 126, 128. Because of the larger radius R2 of the second scan circle 124, the set of points defined by the intersection of the second family of cones, including cones 126, 128, is displaced in the negative Z direction relative to the region imaged when the X-ray source 32 follows the path 114 (FIG. 4a). Thus, the object plane 74 is lowered by an amount $\Delta Z$ to the second plane 112, and the image region is substantially centered about the arrow pattern 70. As the X-ray spot 32 and detector 16 rotate, a distinct image 130 of the arrow pattern 70 is then produced on the detector 16, while the image of the cross pattern 72, lying outside the object plane 74, appears blurred. The amplitude of the gain adjustment made to the voltages applied to the deflection coils 60, 62 is proportional to the direction and amount of the shift $\Delta Z$ in the object plane 74. For example, a large increase in the gain would result in a relatively large movement of the image plane 74 in the downward (i.e., negative Z) direction, while a small decrease in the gain would result in a relatively small movement of the image plane 74 in the upward (i.e., positive Z) direction. In this manner, the geometry utilized in the laminographic system of the present invention further allows various planes in the object 14 to be imaged upon the detector 16 without mechanical movement of any of the system components.

Figure 5B:
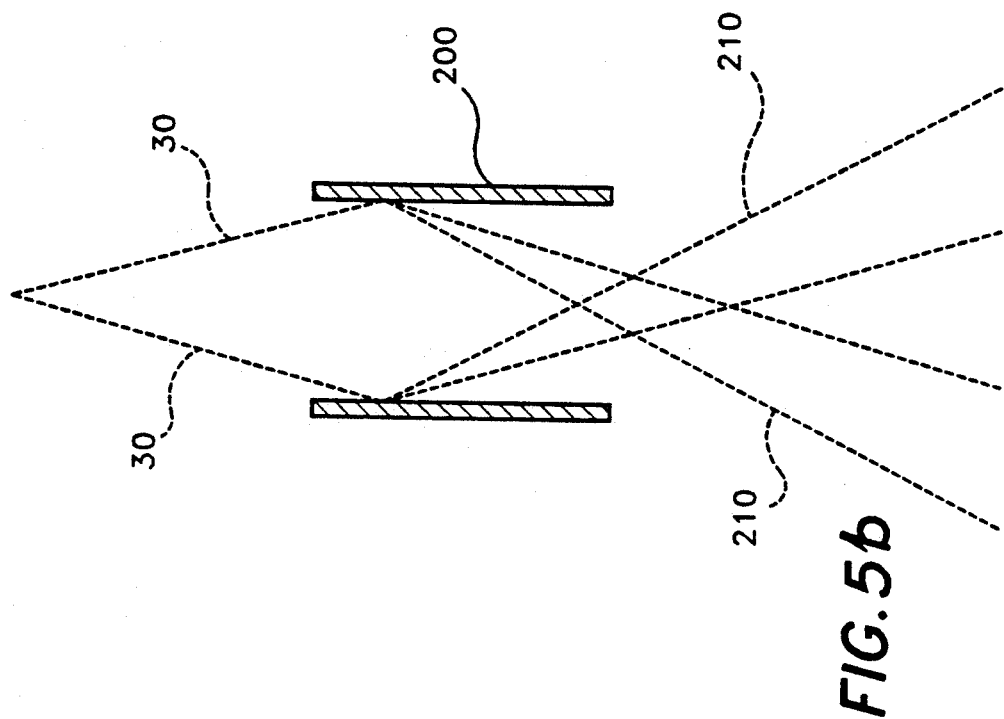
FIGS. 5a, 5b and 6 illustrate possible embodiments of a target that may be used in accordance with present invention.
Figure 5A:
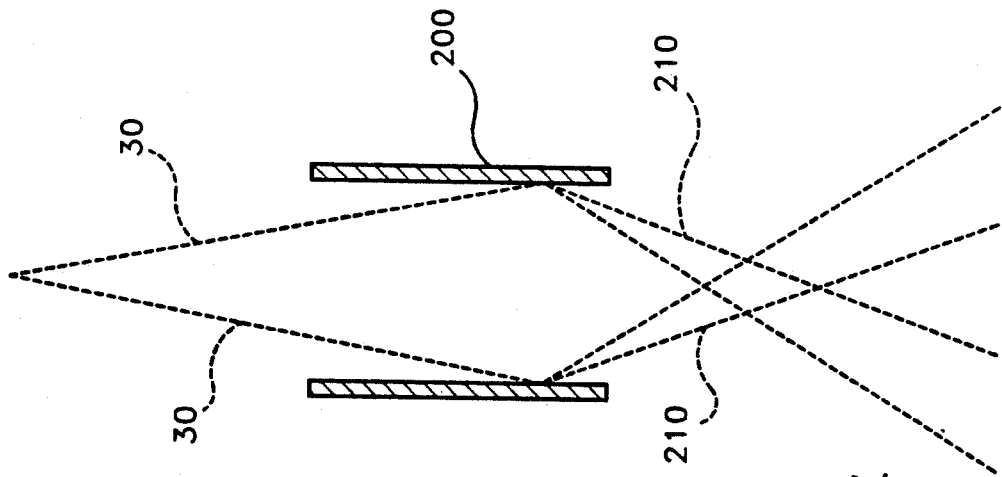
Figure 6:
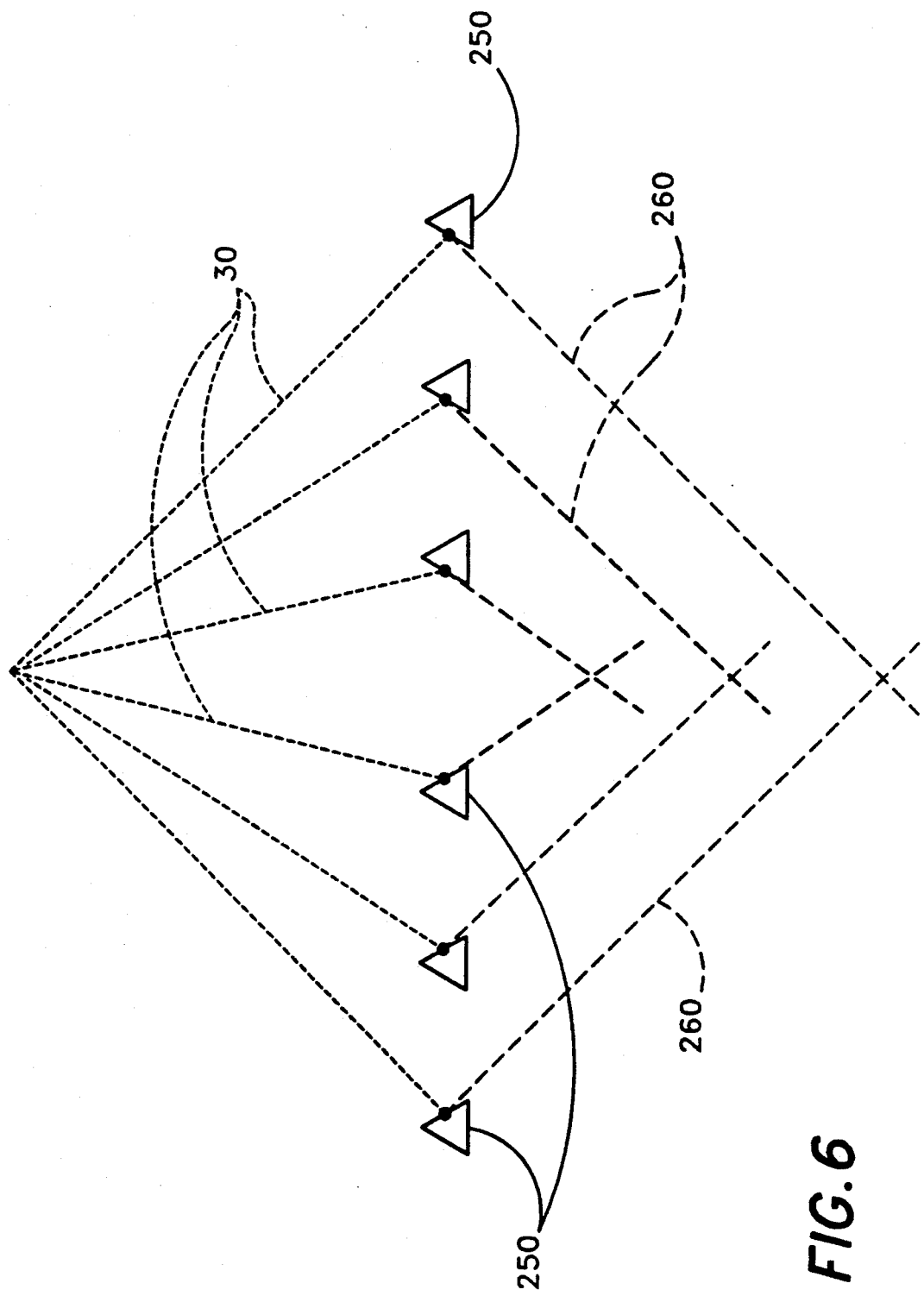

It will be understood that different configurations of the target anode 24 may be used in accordance with the present invention. For example, FIGS. 5a, 5b and 6 illustrate two possible embodiments of a target that may be used in accordance with the present invention. In FIGS. 5a and 5b, a cross-sectional view of an alternative target 200 is shown. The target 200 is constructed as a hollow cylinder which has a coating of tungsten, or similar material, on its inner surface. As shown in FIG. 5a, when the electron beam 30 is deflected in a circular pattern so that it strikes the interior surface of the target 200, X-rays 210, which are incident upon the detector, are emitted from the spots where the electron beam 30 strikes the target 200 so that the X-rays intersect in the focal plane 74. When the path traced by the electron beam 30 is moved vertically up to another portion of the interior of the target 200, as shown in FIG. 5b, the X-rays 210 are emitted so that they intersect in another focal plane 74 that is vertically displaced in the positive Z direction from the focal plane defined by the X-rays shown in FIG. 5a. Thus, distinct focal planes can be defined along the Z axis using the configuration of the target 200 shown in FIGS. 5a and 5b.

FIG. 6 shows a cross-sectional view of another embodiment of the target. In the embodiment shown in FIG. 6, a target 250 comprises multiple concentric rings which are formed so that X-rays 260 are produced when the electron beam 30 is incident upon the surface of the target 250. Each of the rings has a different radius so that objects in different focal planes along the Z axis are imaged when the electron beam 30 is deflected to trace a path on selected ones of the rings of the target 250.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:
1. A laminography system comprising:
   an X-ray source adapted for emitting X-rays from a moving point, said X-ray source further comprising:
      a source of electrons for producing a beam of electrons;
      a target anode for converting said beam of electrons into an X-ray source when said beam of electrons impinges upon said target anode;
      an electromagnetic deflector for electronically deflecting said beam of electrons onto said target anode along a first predetermined path about a first designated location such that X-rays are emitted from a moving point which follows said first predetermined path about said first designated location;
   a planar X-ray detector adapted to move along a predetermined path which is coordinated with said first predetermined path of said X-ray source to produce a laminographic image of a first field of view of an image plane within an object being inspected; and
   a control system for regulating and directing said electromagnetic deflector to deflect said beam of electrons onto said target anode along a second predetermined path about a second designated location such that X-rays are emitted from a moving point which follows said second predetermined path about said second designated location, said second predetermined path coordinated with said planar X-ray detector predetermined path to produce a laminographic image of a second field of view of the image plane within the object without altering either the position of the object or said predetermined path of said X-ray detector.

2. A laminography system as defined in claim 1, wherein said X-ray source first predetermined path is circular, and said first designated location is the center of rotation of said circular path.

3. A laminography system as defined in claim 1, wherein said control system comprises a look-up-table (LUT).

4. A laminography system comprising:
an X-ray source which emits X-rays from a moving point, said X-ray source further comprising:
a source of electrons for producing a beam of electrons;
a target anode for converting said beam of electrons into an X-ray source when said beam of electrons impinges upon said target anode;
an electromagnetic deflector for electronically deflecting said beam of electrons onto said target anode along a predetermined first circular path about a center of rotation, said first circular path having a first radius;
an X-ray detector coordinated with said X-ray source so that a first field of view is defined wherein a first cross-section image of an object placed in said first field of view is produced by the detector; and
a control system for regulating and directing said electromagnetic deflector to deflect said beam of electrons onto said target anode to cause said moving point of said X-ray source to rotate in a second circular path about said center of rotation, said second circular path having a second radius, so that a second field of view is defined wherein a second cross-section image of said object placed in said second field of view is produced by the detector, thereby producing images of said object from said first and said second fields of view without altering either the location of said object or said detector.

5. A laminography system as defined in claim 4 wherein said control system comprises a look-up-table (LUT).

6. A method of producing a laminographic image comprising the steps of:
generating a source of X-rays which follows a predetermined path about a designated point, said generating step further comprising the steps of:
producing a beam of electrons;
directing said beam of electrons into a target anode thereby producing said X-rays;
electronically deflecting said beam of electrons to follow said predetermined path about said designated point;
coordinating an X-ray detector with said moving X-ray source so that a field of view is defined in an object plane wherein a cross-sectional image of an object placed in the field of view is produced by the detector;
maintaining the configurations of said X-ray detector and said object; and
electronically shifting the designated point about which said predetermined path of said beam of electrons follows, thus shifting the designated point about which said X-ray source travels, thereby shifting the location of said field of view in said object plane.

7. A method of producing a laminographic image as defined in claim 6, wherein said X-ray source is moved along a circular path, and said designated point is defined as the center of rotation of said circular path.

8. A method of producing a laminographic image comprising the steps of:
generating a source of X-rays which follows a predetermined first circular path about a center of rotation, said first circular path having a first radius, said generating step further comprising the steps of:
producing a beam of electrons;
directing said beam of electrons into a target anode thereby producing said X-rays;
electronically deflecting said beam of electrons to follow said predetermined first circular path about said center of rotation;
coordinating an X-ray detector with said rotating X-ray source so that a field of view is defined in an object plane wherein a cross-sectional image of an object placed in the field of view is produced by the detector;
maintaining the configuration of said X-ray detector and said object; and
electronically changing the radius of rotation of said X-ray source thereby causing said X-ray source to rotate in a second circular path about said center of rotation, said second circular path having a second radius, thereby shifting the location of said field of view.

9. A laminography system comprising:
a moving source of X-rays, said moving source of X-rays further comprising:
a source of electrons for producing a beam of electrons;
a target anode for converting said beam of electrons into an X-ray source when said beam of electrons impinges upon said target anode;
an electromagnetic deflector for electronically deflecting said beam of electrons onto said target anode along a predetermined path such that X-rays are emitted from a moving point which follows said predetermined path;
an X-ray detector having an image area which is coordinated with said moving source of X-rays;
means for supporting an object to be inspected in a stationary position located between said moving source of X-rays and said detector; and
a control system comprising:
a driver for driving said moving source of X-rays along said predetermined path;
a coordinator for coordinating the motion of said moving source of X-rays with said detector in a manner which produces a laminographic image having a field of view in an object plane of the object under inspection; and
a field of view shifter for altering said predetermined path followed by said moving source of X-rays thereby moving the field of view and producing a laminographic image of a different portion of the object without changing the configuration of either the object or the detector.

10. A laminography system comprising:
a source of X-rays adapted for emitting X-rays from a moving point, said source of X-rays further comprising:
a source of electrons for producing a beam of electrons;
a target anode for converting said beam of electrons into an X-ray source when said beam of electrons impinges upon said target anode;
an electromagnetic deflector for electrically deflecting said beam of electrons onto said target anode along a first circular path about a center of rotation, said first circular path having a first radius;

an X-ray detector having an image area which is adapted to move along a predetermined path which is coordinated with said first circular path of said X-ray source to produce a laminographic image of a portion of a first image plane within an object being inspected; and a control system for regulating and directing said electromagnetic deflector to deflect said beam of electrons onto said target anode to rotate said X-ray source in a second circular path about said center of rotation, said second circular path having a second radius, thereby producing a laminographic image of a portion of a second image plane within the object without altering either the position of the object or the path of the detector image area.

11. A laminography system comprising:

a moving source of X-rays, said moving source of X-rays further comprising:
- a source of electrons for producing a beam of electrons;
- an electromagnetic deflector for electronically deflecting said beam of electrons;
- a target anode for converting said beam of electrons into an X-ray source when said beam of electrons impinges upon said target anode, said target anode having a plurality of concentric rings wherein said deflector deflects said electron beam to a specific concentric ring;

an X-ray detector which is coordinated with said moving source of x-rays to produce a laminographic image of a first portion of an image plane within an object to be inspected when said moving source of X-rays is from a first one of said concentric rings; and a control system for deflecting said beam of electrons onto said target anode so that a selected circular path, corresponding to a second one of said concentric rings of said target anode, is traced by said moving source of X-rays, thereby producing a laminographic image of a second portion of said image plane within the object without altering the position of the object or the configuration of the detector, the change in position of said image plane from said first portion to said second portion being determined by the selection of said first and second concentric rings of said X-ray target anode, respectively.

12. A laminography system comprising:

a moving source of X-rays, said moving source of X-rays further comprising:
- a source of electrons for producing a beam of electrons;
- an electromagnetic deflector for electronically deflecting said beam of electrons;
- a target anode for converting said beam of electrons into an X-ray source when said beam of electrons impinges upon said target anode, said target anode being formed to have a cylindrical interior surface about a central axis;

an X-ray detector which is coordinated with said moving source of X-rays to produce a laminographic image of a portion of a first image plane within an object to be inspected when said deflector deflects said electron beam to a first location along said central axis; and a control system for deflecting said beam of electrons onto a second location along said central axis of said cylindrical interior surface of said target anode, thereby producing a laminographic image of a portion of a second image plane within the object without altering the position of the object or the configuration of the detector, the change in position of said laminographic image from said first image plane to said second image plane being determined by the selection of said first and second locations along said central axis of said circular path of said moving source of X-rays.

13. A laminography system comprising:

a moveable source of penetrating radiation, said moveable source further comprising:
- a source of electrons for producing a beam of electrons;
- a target anode for converting said beam of electrons into an X-ray source when said beam of electrons impinges upon said target anode; and
- an electromagnetic steering device for electronically controlling the motion of said source;

an imaging system for producing a cross-sectional image of a cutting plane of an object, said imaging system comprising:
- a radiation detector having a variable position image forming region wherein the position of said image forming region is monitored by a position sensor which transmits coordinates corresponding to its position; and
- a detector control system which receives said coordinates from said sensor and transmits corresponding signals to said steering device thus causing said motion of said radiation source to be synchronized with said motion of said image forming region; and a field of view controller, connected to said steering device, for selecting first and second fields of view for said cross-sectional image of a cutting plane of said object, wherein said first field of view is produced when said controller causes said steering device to move said source of penetrating radiation along a first predetermined path having a first reference point and said second field of view is produced when said controller causes said steering device to move said source of penetrating radiation along a second predetermined path having a second reference point.

14. An apparatus as defined in claim 13 wherein said field of view of controller further comprises a position controller for positioning said first and second predetermined path reference points.

15. An apparatus as defined in claim 14 wherein said position controller further comprises an X-Y plane shifter for positioning said first and second predetermined path reference points at different points in an X-Y plane thus producing said first and second fields of view cross-sectional images of a cutting plane of said object at different locations of said X-Y plane.

16. An apparatus as defined in claim 15 wherein said X-Y plane shifter further comprises a deflection device.

17. An apparatus as defined in claim 13 wherein said field of view controller further comprises a path shape controller for shaping said first and second predetermined paths.

18. An apparatus as defined in claim 17 wherein said path shape controller further comprises a path size controller for producing first and second predetermined paths having substantially the same shape and different sizes thus producing said first field of view cross-sectional image of a first cutting plane of said object and said second field of view cross-sectional image of a second cutting plane of said object.

19. An apparatus as defined in claim 18 wherein said path shape controller further comprises a gain device.

20. A laminography system comprising:
a moveable source of penetrating radiation, said moveable source further comprising:
   a source of electrons for producing a beam of electrons;
   a target anode for converting said beam of electrons into an X-ray source when said beam of electrons impinges upon said target anode; and
   an electromagnetic steering device for electronically controlling the motion of said source along a predetermined path;
an imaging system, coordinated with said moveable source of penetrating radiation, for producing a cross-sectional image of a cutting plane of an object located adjacent said moveable source and said imaging system such that radiation from said source passes through said object before reaching said imaging system; and
a field of view controller for producing first and second fields of view of said cross-sectional image of a cutting plane of said object solely by controlling the configuration of said source predetermined path.

* * * * *